(12) United States Patent
Brodaczewski et al.

(10) Patent No.: US 11,439,407 B2
(45) Date of Patent: Sep. 13, 2022

(54) LAPAROSCOPIC CLIPPING MACHINE FOR APPLICATION OF SURGICAL CLIPS ON TISSUE STRUCTURES

(71) Applicant: KONMEX LIMITED LIABILITY COMPANY, Józefów (PL)

(72) Inventors: Wieslaw Brodaczewski, Brentford (GB); Konrad Brodaczewski, Balbriggan (IE); Thomasz Przekopiński, Ząbki (PL)

(73) Assignee: KONMEX LIMITED LIABILITY COMPANY, Józefów (PL)

( * ) Notice: Subject to any disclaimer, the term of this patent is extended or adjusted under 35 U.S.C. 154(b) by 31 days.

(21) Appl. No.: 16/849,684

(22) Filed: Apr. 15, 2020

(65) Prior Publication Data

US 2020/0330102 A1 Oct. 22, 2020

(30) Foreign Application Priority Data

Apr. 18, 2019 (PL) .......................................... 429691

(51) Int. Cl.
*A61B 17/128* (2006.01)
*A61B 17/29* (2006.01)

(52) U.S. Cl.
CPC .......... *A61B 17/1285* (2013.01); *A61B 17/29* (2013.01); *A61B 2017/2913* (2013.01); *A61B 2017/2927* (2013.01); *A61B 2017/2933* (2013.01)

(58) Field of Classification Search
CPC ................ A61B 17/1285; A61B 17/29; A61B 2017/2913; A61B 2017/2927; A61B 2017/2933; A61B 2017/2932; A61B 2017/2924; A61B 2017/2925; A61B 2017/2926; A61B 2017/2934; A61B 2017/2936; A61B 2017/2947
See application file for complete search history.

(56) References Cited

U.S. PATENT DOCUMENTS 5,810,240 A * 9/1998 Robertson ............ A61B 17/072
227/175.2
2019/0000482 A1 1/2019 Hu et al.

* cited by examiner

*Primary Examiner* — Brooke Nicole Labranche
(74) *Attorney, Agent, or Firm* — Maschoff Brennan

(57) ABSTRACT

A laparoscopic clipping machine that is used to apply clips on tissue structures is enclosed in a housing and includes a pair of movable jaws mounted on a stem. Operational movement for clamping the clips is indirectly triggered by a movement of the handle. The clipping machine further includes at least one spring and a mechanism directly triggering the operational movement of the jaws having at least one pusher movably arranged in the axis of the stem supported in the axis of the stem on the spring. An adjustment mechanism adjusts the jaws output opening to at least two different positions adapted to at least two sizes of the clips, resulting in a different output angle between the jaws, wherein the adjustment mechanism includes a movable shutter element having at least two parts, the narrower part of the shutter element and the wider part of the shutter element.

14 Claims, 18 Drawing Sheets

Figure 1:
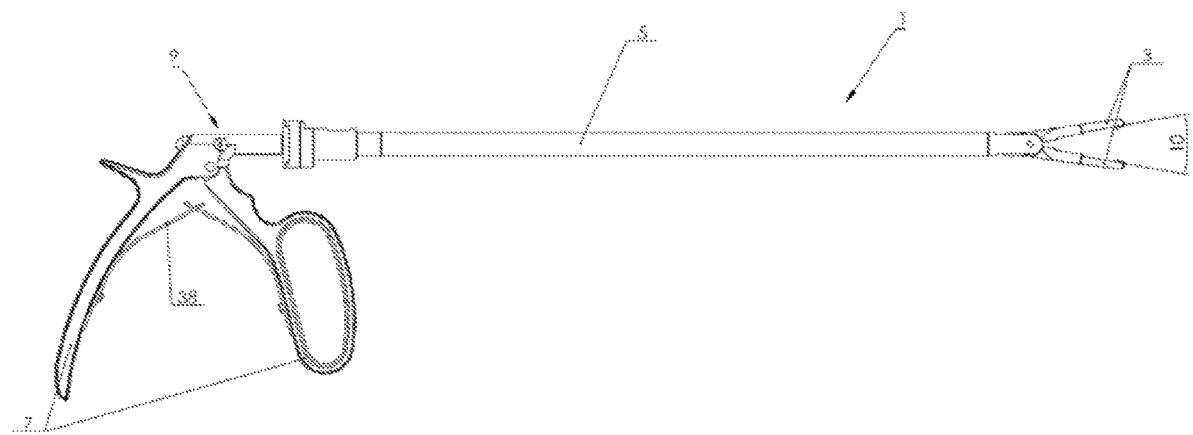

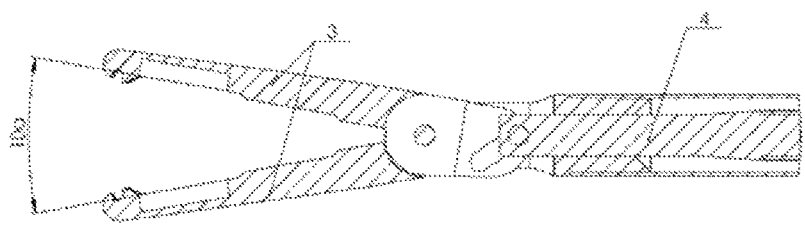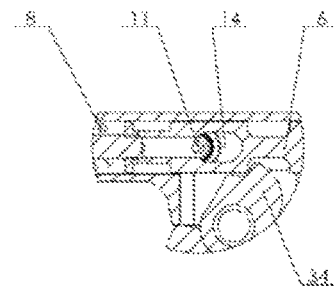
Fig. 3a
Fig. 3b

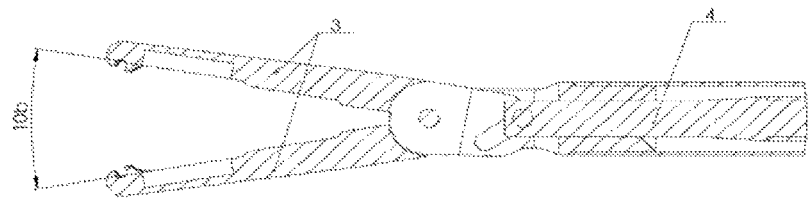 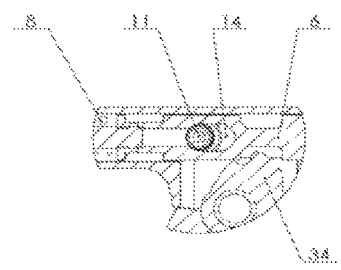
Fig. 4a                    Fig. 4b

LAPAROSCOPIC CLIPPING MACHINE FOR APPLICATION OF SURGICAL CLIPS ON TISSUE STRUCTURES

The subject of the invention is the laparoscopic clipping machine adapted for application of different sizes of clamps—surgical clips, on tissue structures.

Endoscopic surgical clipping machines are known, where the end effector is a moving jaw that opens and closes. Known clipping machines comprises two main elements: the handgrip and the endoscopic part—the stem—the tubular part terminated with an effector in the form of two jaws. Known laparoscopic clipping machines for application of clips on tissue structures comprises a pair of movable jaws mounted at the end of the enclosed stem, a mechanism that triggers the operational movement of the jaws in the form of at least one pusher movably located inside the stem, located in the stem axis, which is moved by a trigger mechanism located in the stem—most often spring arrangement. The trigger mechanism comprises a fixed handle and a movable handle. When the movable handle is clamped, the pusher moves and the jaws close. The spring located in the fixed handle causes the movable handle to return to the output position and opens the jaws. The clipping machine can comprise one or several pushers in each handgrip-structure and several in the stem. Indirectly, the operational movement of the jaws is triggered by moving the movable element of the handgrip—the handle associated with one of the springs and thus with the pusher. This movement—closing and opening the jaws is an operational movement of the jaws and enables clamping the clips in the jaws. After activating the device—simultaneously the movement of the handle, the spring relieves the handle to its original position—not active and closes the jaws. Movement of the handle compresses the spring, and spring returns to its original position. Spring opens the jaws. The mechanism triggering the jaws to move in two positions—closed jaws—open jaws, does not allow the clips to be changed to larger or smaller size because jaws move with a fixed opening range—the angle between the jaws, which significantly limits the operation performed during surgical procedures. It causes, that a specific clipping machine is adapted only to one type of clip. It also requires the use of several clipping machines instead of one if it is necessary to use a different clip during the surgery, which prolongs the surgical procedure.

There are also known automatic laparoscopic clipping machines of different design than the so-called manual ones. In the case of a "manual" clipping machine, the clips are taken manually one by one, and in the case of an automatic clipping machine, several clips are stored in the clipping machine magazine, e.g. 20 clips, and the clips are fed to the jaws automatically.

From the description of the invention US20190000482, an automatic clipping machine with an endoscopic part is known, the handgrip of which includes an inner housing, a handle—a mechanism that activates the movement of the jaws, the mechanism of which is associated with the pusher through a spring arrangement. The handle is connected to the hinge by the handle spring. Movement of the handle is transferred to a movable hinge, the extraction of which makes the pusher move longitudinally. The arrangement includes several different springs connected to each other, while the pressure of one of the springs with a different coil spacing on another spring with a fixed coil spacing prevents the pusher from moving backwards, which gives it the possibility of adjustment its output opening.

However, automatic clipping machines have some disadvantages related to cost and the possibility of blocking the feeding system. Due to the frequent need for different clips sizes to be applied during a single surgical operation, convenient solutions for manual clippers are still being sought, giving the possibility of quick but also precise change of the jaws output opening angle, to which various types of clips are adapted. This operation should be ensured without changing the type of clipping machines adapted to different jaws output openings, which are adapted to different types (sizes) of clips.

New, easier and more reliable and more stable solutions are still being sought for the regulation of the jaws of non-automatic clipping machines.

Therefore, the subject of the invention is a non-automatic clipping machine, which makes it possible, from the point of view of the device operator and the precise design to be made, a system for adjustment the jaws output opening—change of the jaws output opening angle, which is adapted to different sizes of clips.

The laparoscopic clipping machine for application of clips on tissue structures according to the invention is characterised in that, in addition to the mechanism for operative movement of the jaws, it includes a mechanism that adjusts the opening of the jaws to at least two different positions of the jaws output opening adapted to at least two sizes of clips, resulting in a different output angle between the jaws. The output opening is given indirectly by the movement of the handle. The adjustment mechanism comprises the movable shutter element in different embodiments. This element has two parts: the narrower part of the shutter element and the wider part of the shutter element. The shutter element is movably guided through a transverse through opening formed in the pusher, which is larger than a wider part of the shutter element, so that the shutter element, when seated in the through opening of the pusher, partially covers the through opening light of the pusher, thus limiting the movement of the pusher when determining an output angle, in such a way, that after passing through the pusher through opening of the narrower part of the shutter element a partially limited longitudinal movement of the pusher is obtained, resulting in the first output angle, and after passing the wider part of the shutter element and its location in the through opening light, a significantly limited longitudinal movement of the pusher is obtained, resulting in the second output angle. It is also possible to supply the shutter element with several parts of different widths, obtaining different jaws output opening angles.

Preferably, the through opening is oval in the longitudinal cross-section, where the oval is characterised by a shorter diameter and a longer diameter, where the longer diameter of the oval is directed along the axis of the pusher and the shorter diameter of the oval is perpendicular to the axis of the pusher, and then the longer diameter of the oval is longer than the widest part of the shutter.

In first embodiment, the shutter element has an overall shape of a partial cylinder and cone and has a form of a changing width of a first cylinder extending on one side into a cone with a diameter increasing in relation to the diameter of a second cylinder and then extending into a second cylinder, which is partly guided in a first sleeve made in the clipping machine stem housing. A threaded connection is formed on a lateral surface of a second cylinder extending through a first sleeve and on an inner surface of a first sleeve so that the shutter element is screwed into a first sleeve by passing through a through opening made in the pusher, in such a way, that a second cylinder is screwed into a first sleeve passing through a through opening made in the pusher. When through opening is covered by a movement of the through element, after passing through a through opening light of the of a cylinder, a partially limited longitudinal movement of the pusher is obtained, resulting in the first output angle, while after screwing into a first sleeve of the second cylinder and its passage through a through opening light, a significantly limited longitudinal movement of the pusher is obtained, resulting in the second output angle, and passing through a through opening of the cone, the output angle with a value between the first and the second output angle is obtained.

In second embodiment, the shutter element has an overall shape of a width-graduated cylinder. The movable shutter element is in a form of a third cylinder connected to a fourth cylinder with a larger diameter relative to the third cylinder, wherein the fourth cylinder being movably arranged in a first sleeve made in the clipping machine stem housing. A threaded connection is formed on a lateral surface of the fourth cylinder passing through the first sleeve and on an inner surface of the first sleeve, such that a part of the fourth cylinder is screwed into the first sleeve passing through a through opening made in the pusher. During cover of a through opening by a movement of the through element, after passing through of the pusher through opening light of the third cylinder part, a partially limited longitudinal movement of the pusher is obtained, resulting in the first output angle, and after screwing in the part of the fourth cylinder and its passage through the pusher through opening light, a significantly limited longitudinal movement of the pusher is obtained, resulting in the second output angle.

In third embodiment, the movable shutter element essentially comprises the gripping part mounted on the clipping machine housing and the shutter part permanently connected to the gripping part and the shutter part passes through the pusher through opening light. The shutter part has a shape of a cam with a fixed width and height. The shutter part is movably guided by means of the gripping part in the pusher through opening, so that, after passing a through opening light of the pusher of the shutter part in such a way that the width of the shutter part covers the through opening light, a partially limited longitudinal movement of the pusher is obtained, resulting in the first output angle. After rotating the shutter element, using the gripping part of the shutter element, height of the shutter part covers the through opening light and then a significantly limited longitudinal movement of the pusher is obtained, resulting in the second output angle.

Preferably, the clipping machine comprises at least two movably connected pushers: a first pusher at a height of the handle and a second one extending into the stem with jaws. One end of the first pusher has a spherical seat and the end of the second pusher connected to it has a sphere matching the seat. At a height of the connection of at least two pushers, there is a rotational mechanism causing rotation of the second pusher and the stem relative to the first pusher. The mechanism consisting a knob causing rotational movement of the second pusher and the stem relative to the first pusher, the second sleeve with the knob with which the stem is connected.

The invention allows to obtain a "manual" clipping machine, in which, clips are taken piece by piece from a separate clip magazine, which gives the possibility of precise adjustment of jaws opening—changing the jaws opening angle (output angle), which is adapted to different sizes of clips without changing the type of the clipping machines during surgery.

Figure 2A:
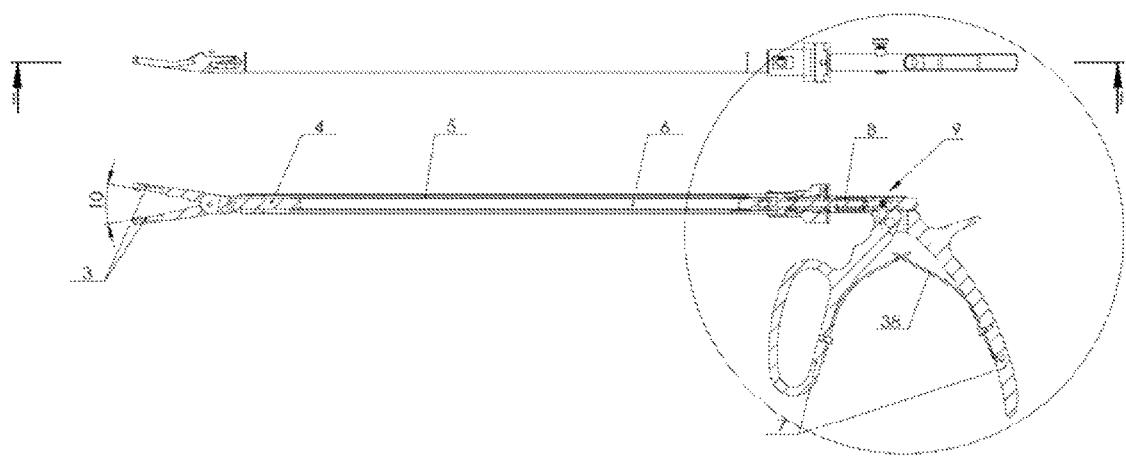
Figure 2B:
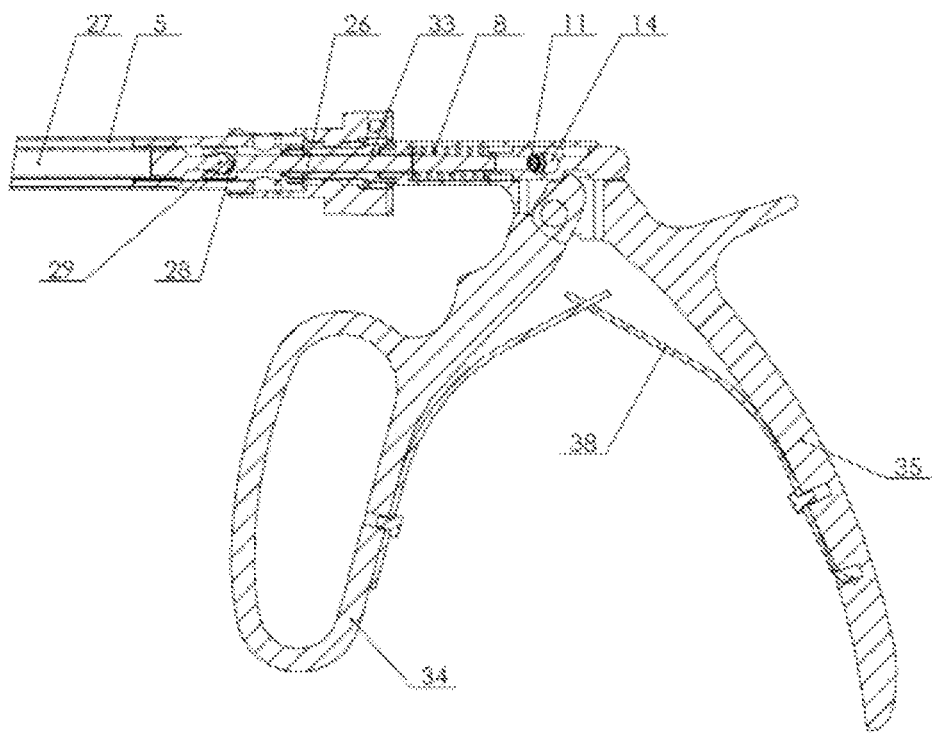
Figure 2C:
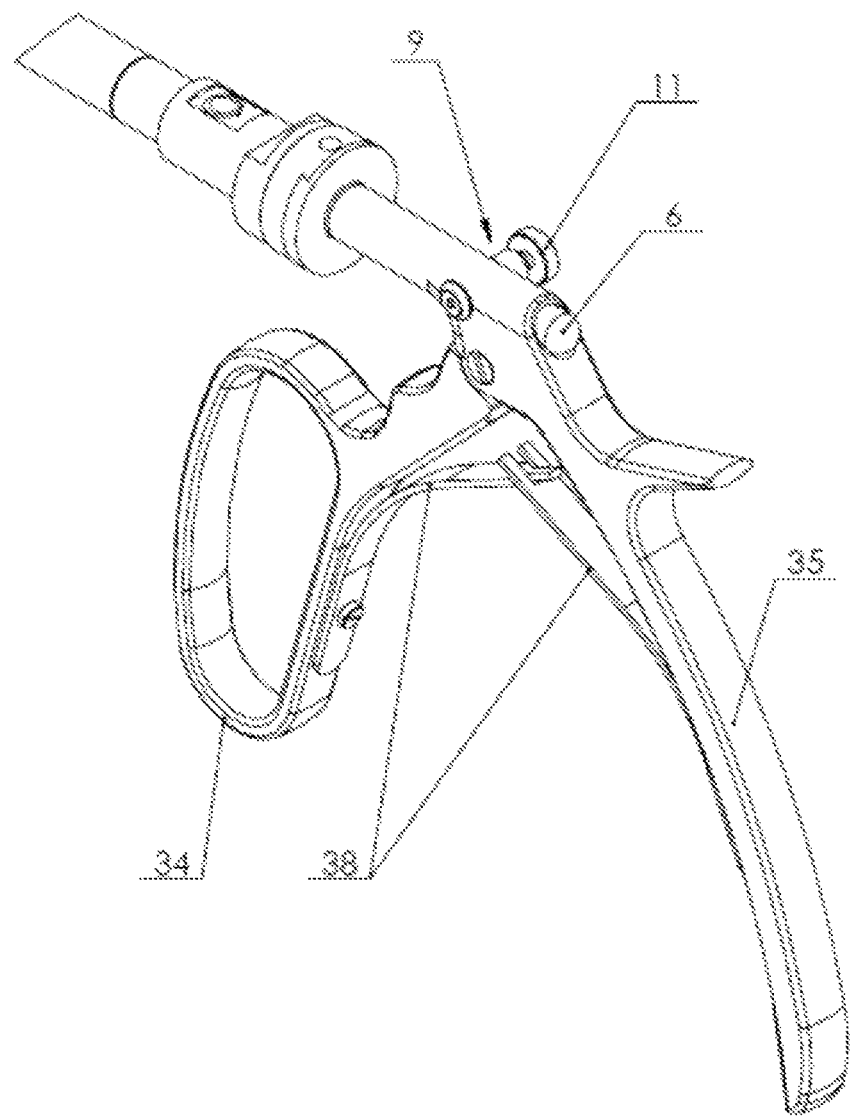
Figure 3C:
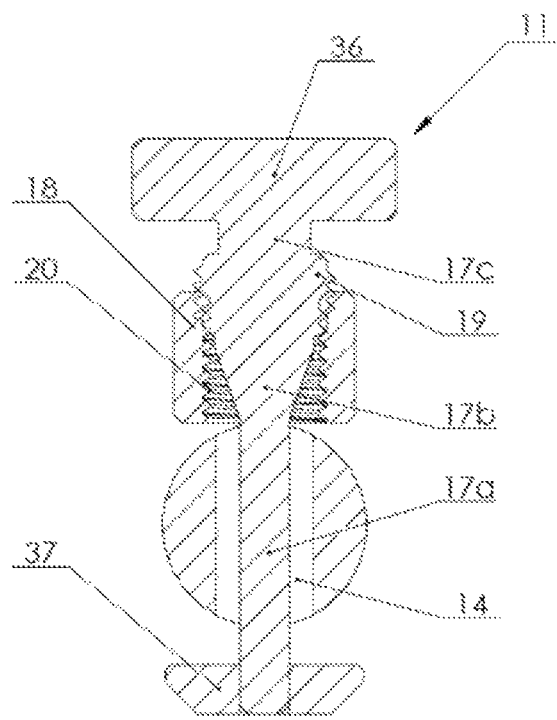
Figure 3D:
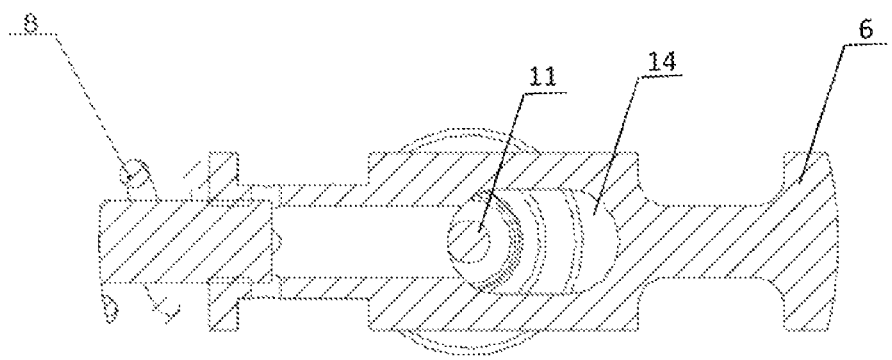
Figure 4C:
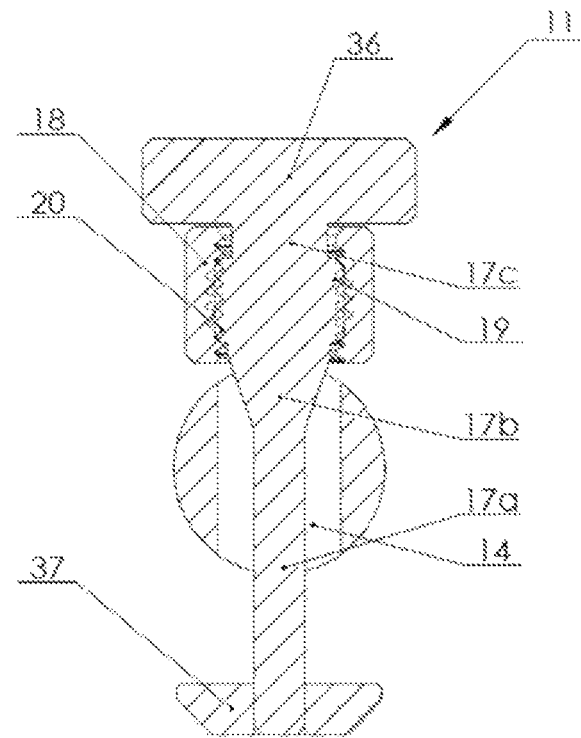
Figure 4D:
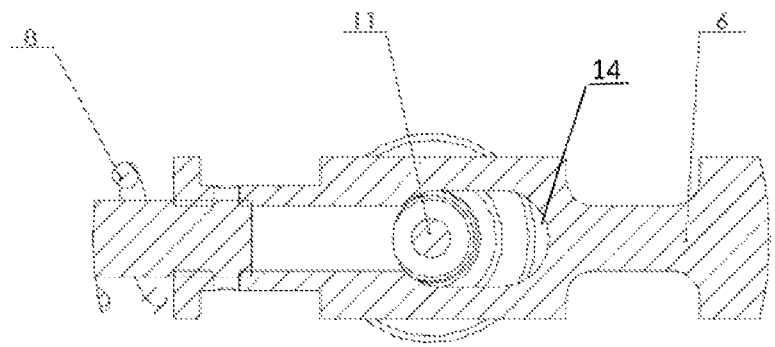
Figure 5A:
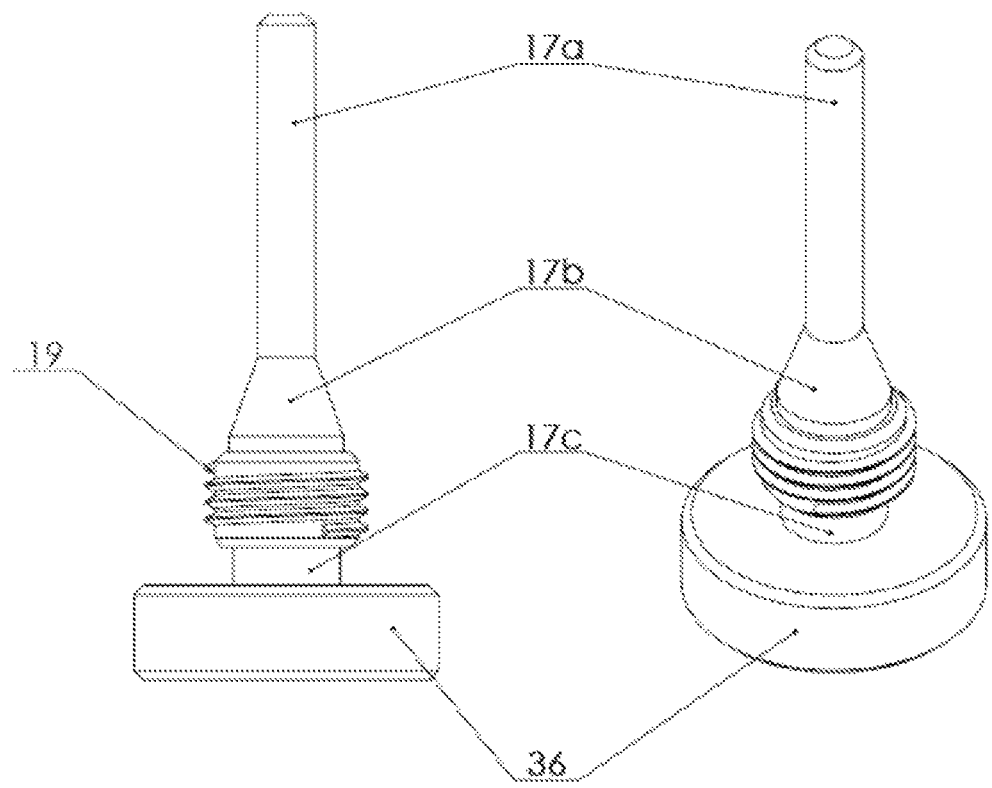
Figure 5B:
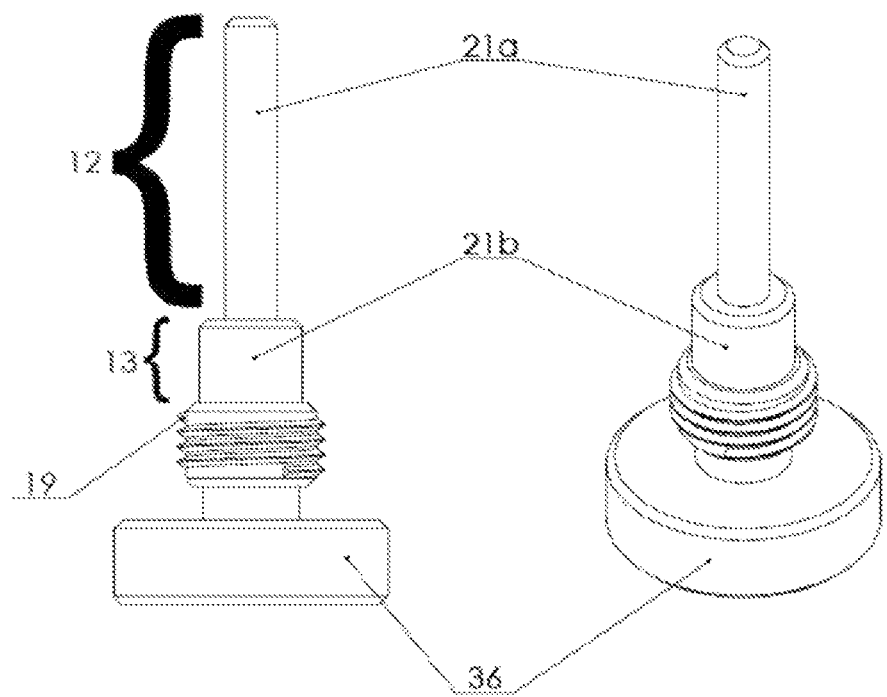
Figure 5C:
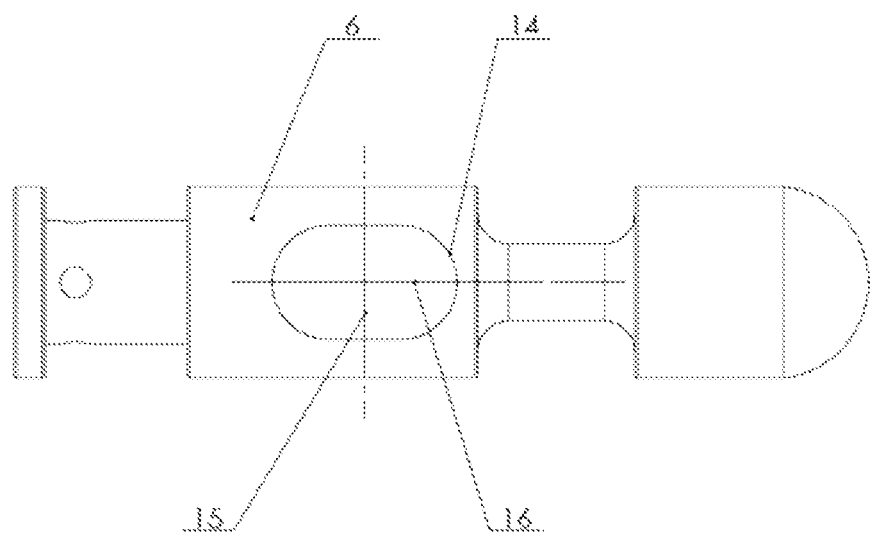
Figure 6:
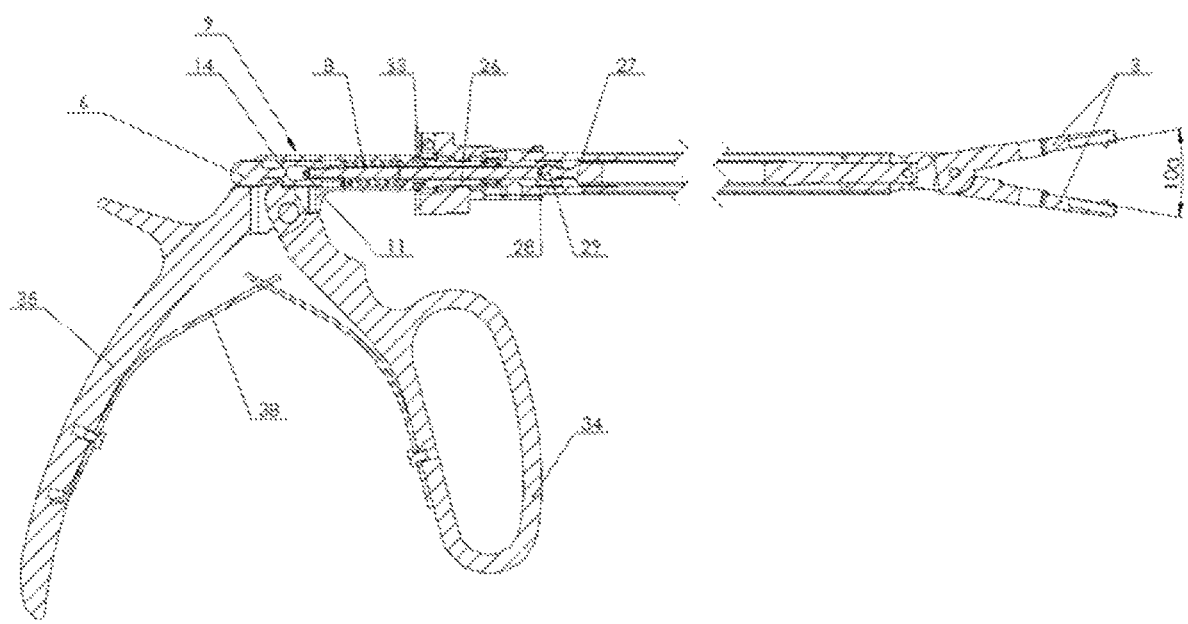
Figure 6A:
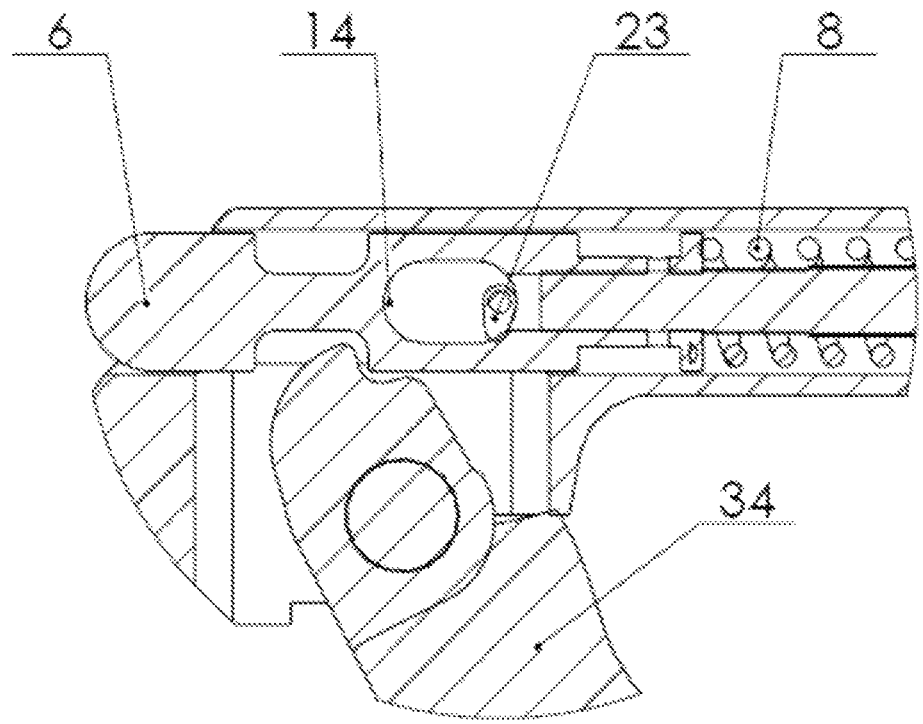
Figure 6B:
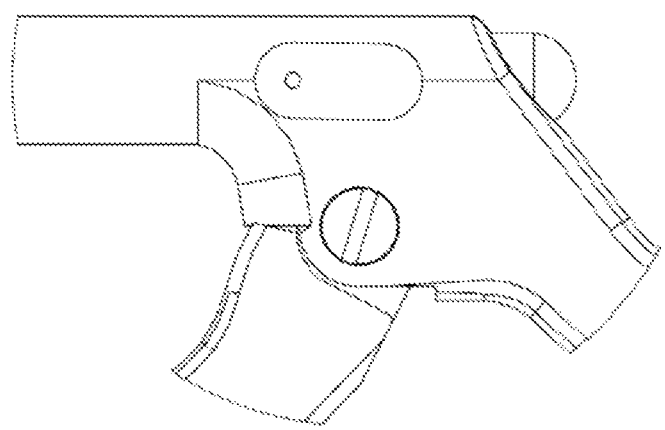
Figure 7:
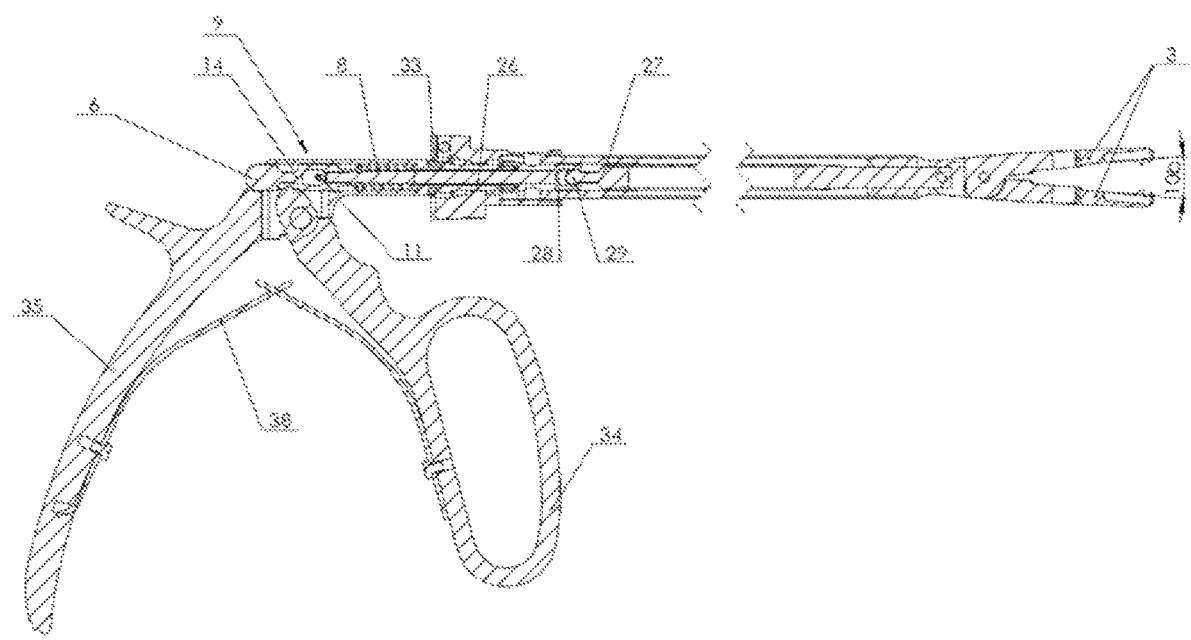
Figure 7A:
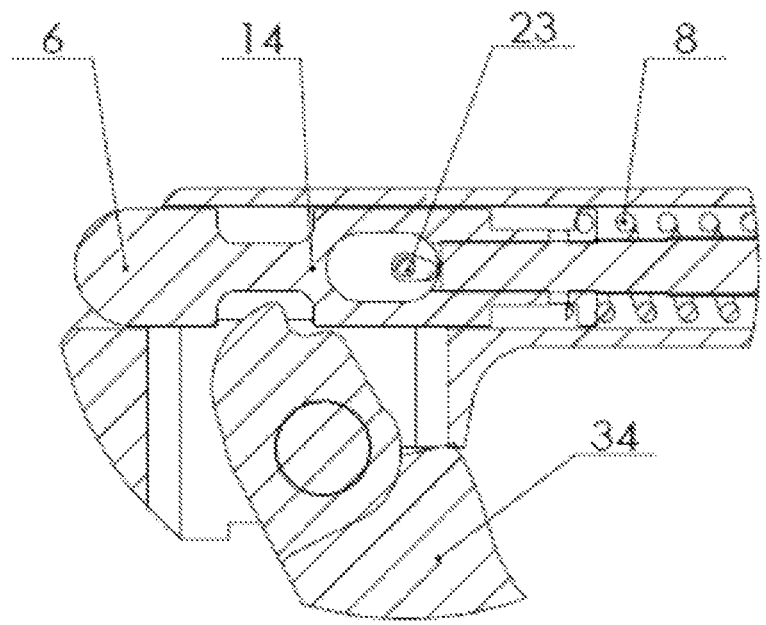
Figure 7B:
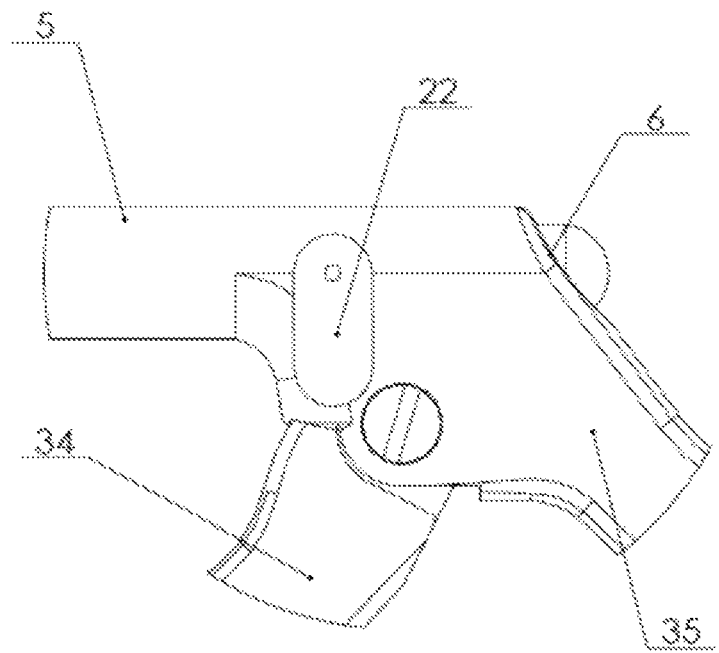
Figure 8:
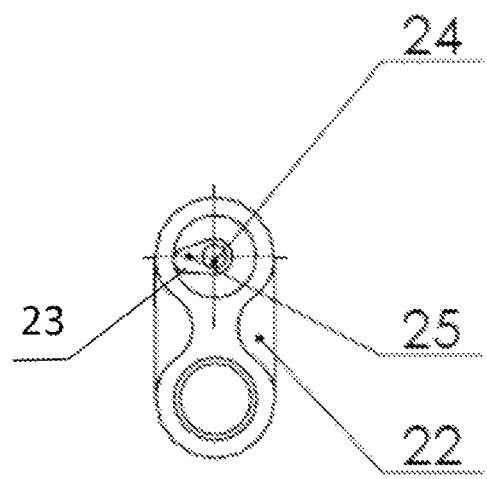
Figure 8A:
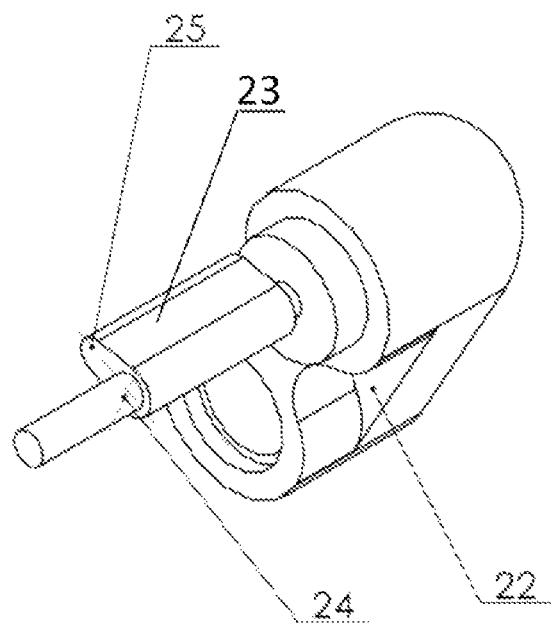
Figure 9:
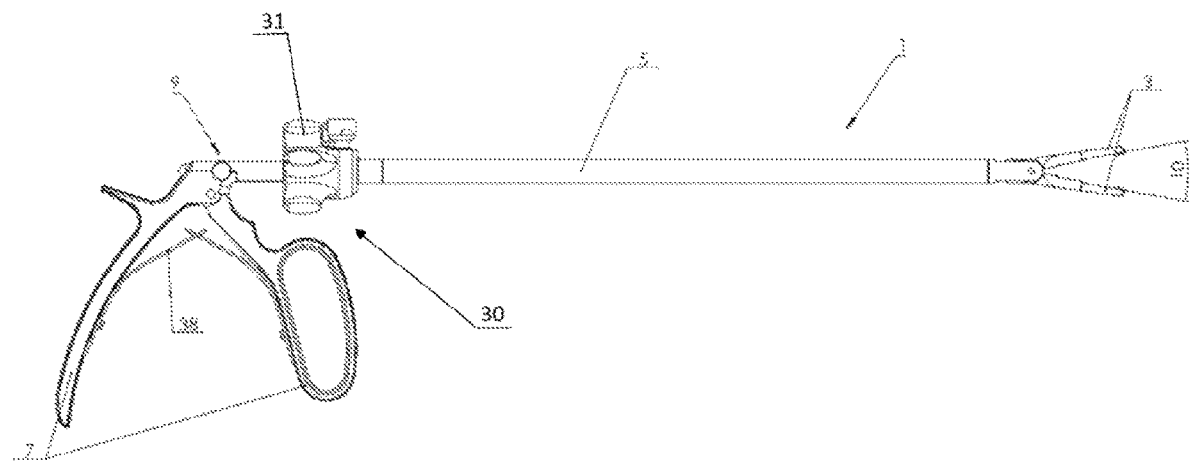
Figure 10:
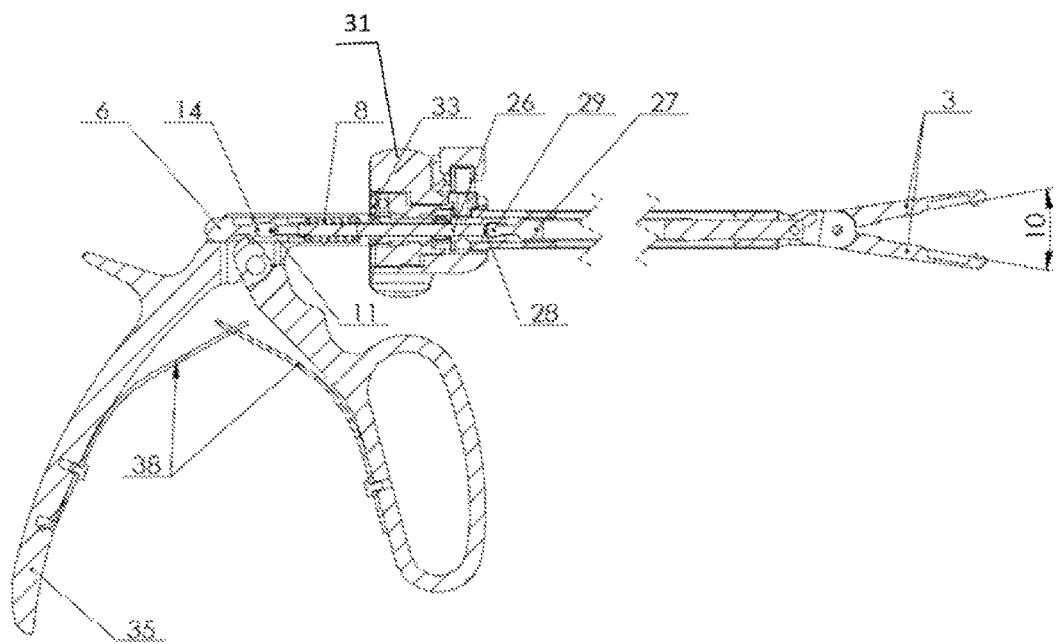
Figure 10A:
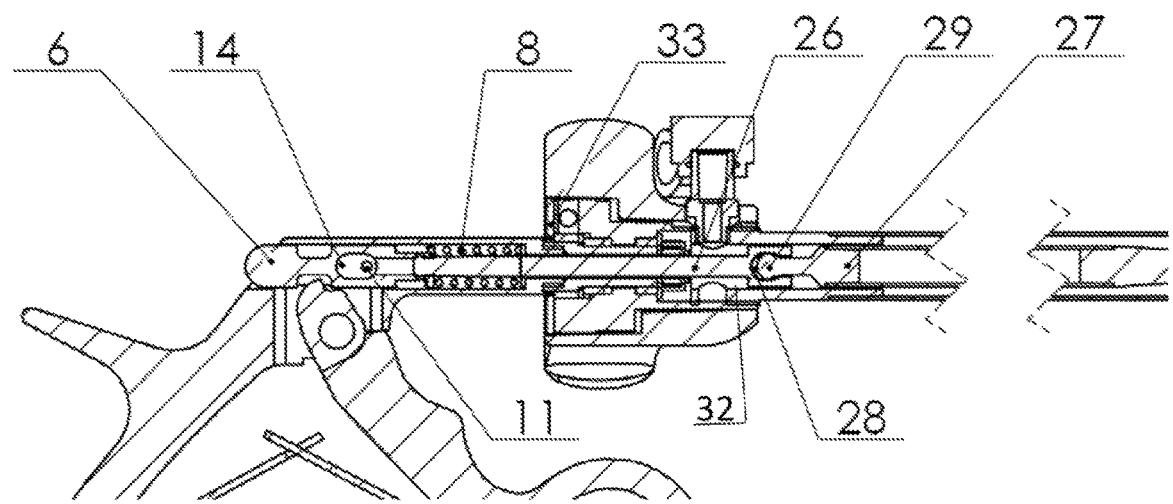
Figure 11:
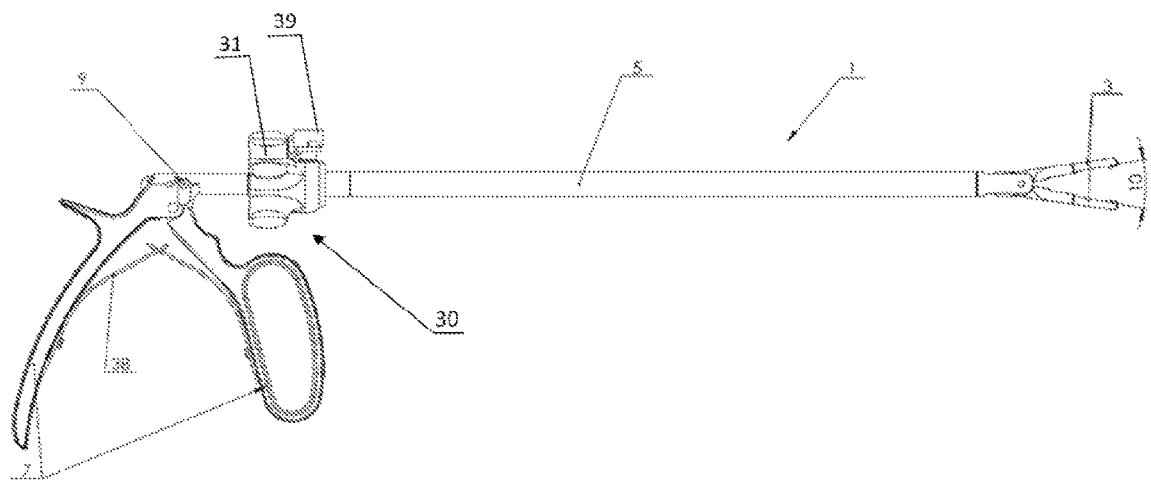
Figure 12:
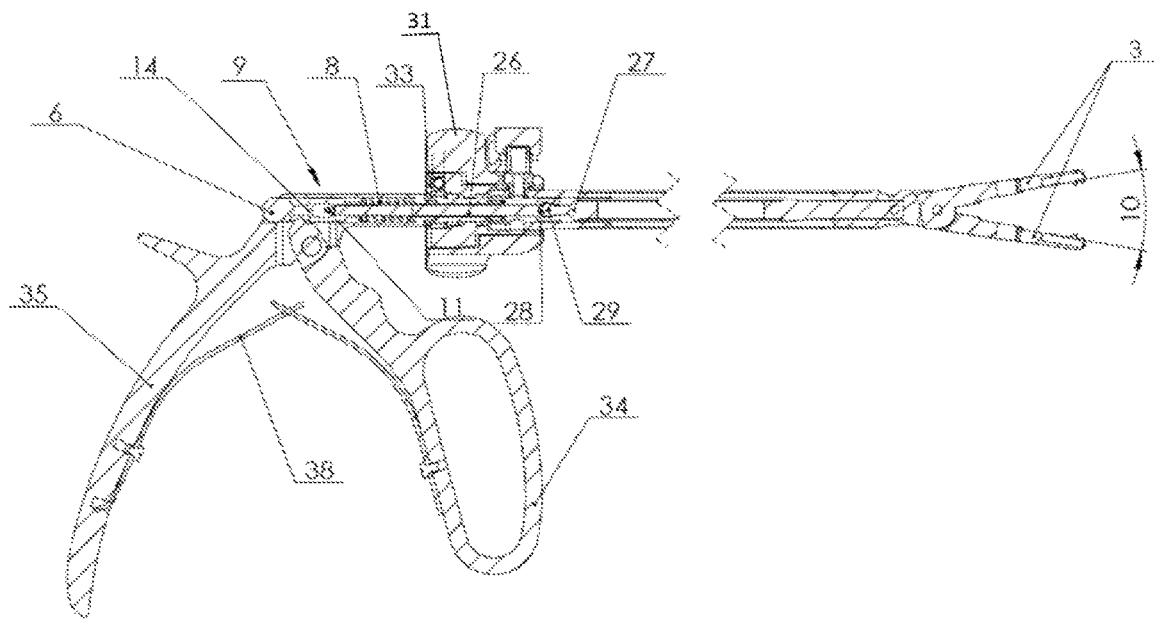
Figure 12A:
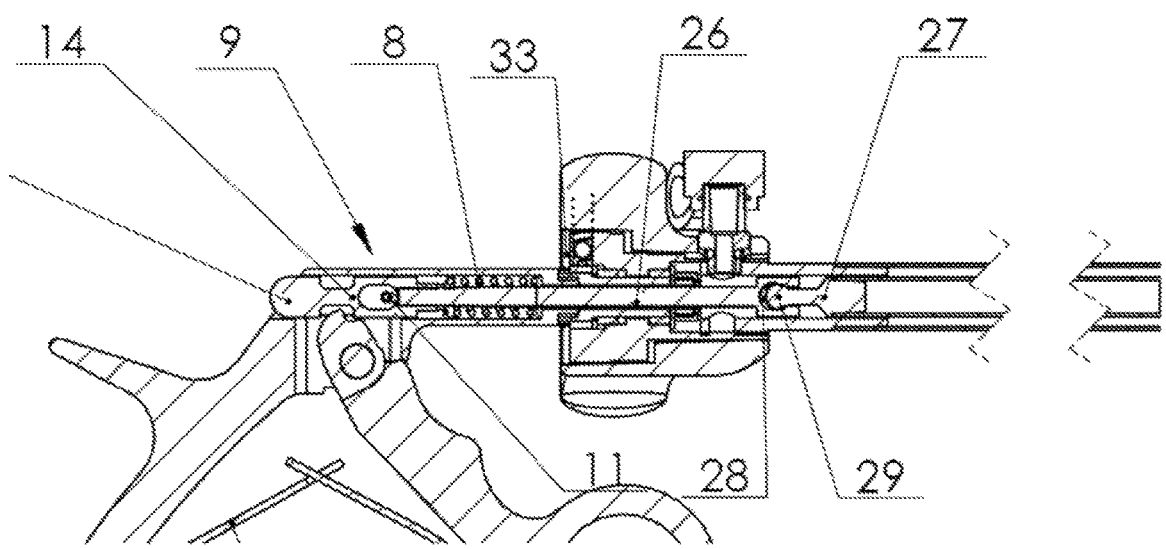

The invention is illustrated in the drawings, in which:

FIG. 1 shows the clipping machine in embodiment where elements are shown from the outside, FIG. 2*a* shows the clipping machine cross-section and its individual parts according to the embodiment of the clipping machine, FIG. 2*b* shows a cross-section of the part of the clipping machine handle in close-up, FIG. 2*c* shows a perspective view of the part of the handle in close-up with the adjustment mechanism for the jaws opening output angle, FIG. 3*a* shows a cross-section through a part of the stem with clipping machine jaws for the first output angle—one of the pre-set jaws opening position A, for the first and second embodiment of the invention, FIG. 3*b* shows, corresponding to the first output angle (as in FIG. 3*a*), the pre-set for jaws opening position A adjustment mechanism, in longitudinal cross-section, for the first and second embodiment of the invention FIG. 3*c* shows a cross-sectional view through the jaws opening adjustment mechanism with the shutter element shown positioned in the pusher opening light for the first output angle—one of the pre-set jaws opening position A (as for FIG. 3*b*), for the first and second embodiment of the invention, FIG. 3*d* shows a longitudinal cross-section through the pusher with the shutter element located in the through opening light corresponding to the first output angle (as in FIG. 3*c*)—the pre-set for jaws opening position A adjustment mechanism, for the first and second embodiment of the invention, FIG. 4*a* shows a cross-section through a part of the stem with the clipping machine jaws for the second output angle—one of the pre-set jaws opening position B, for the first and second embodiment of the invention, FIG. 4*b* shows the pre-set for jaws opening position B adjustment mechanism for corresponding second output angle (as in FIG. 4*a*), in longitudinal cross-section, for the first and second embodiment of the invention, FIG. 4*c* shows a cross-section through the jaws opening adjustment mechanism with the shutter element shown in the pusher opening light, for the second output angle—one of the pre-set jaws opening position B (as for FIG. 4*b*), for the first and second embodiment of the invention, FIG. 4*d* shows a longitudinal cross-section through the pusher with the shutter element located in the through opening light corresponding to the second output angle (as in FIG. 4*c*)—the pre-set for jaws opening position B adjustment mechanism, for the first and second embodiment of the invention, FIG. 5*a* shows two views of the shutter element of the jaws opening adjustment mechanism in the first embodiment, FIG. 5*b* shows two views of the shutter element of the jaws opening adjustment mechanism in the second embodiment, FIG. 5*c* shows a view of the pusher with the through opening made, FIG. 6 shows a cross-section through the clipping machine for the first output angle—one of the pre-set for the jaws opening position A, for the third embodiment of the invention, FIG. 6*a* shows a cross-section through the jaws opening adjustment mechanism, for the first output angle—one of the pre-set jaws opening position A (corresponding to FIG. 6), for the third embodiment of the invention, FIG. 6b shows a view of the clipping machine handgrip part from the gripping side of the shutter element for the pre-set jaws opening adjustment mechanism for the first output angle—one of the pre-set jaws opening position A (corresponding to FIG. 6a), for the third embodiment of the invention, FIG. 7 shows a cross-section through the clipping machine for the second output angle—one of the pre-set jaws opening position B, for the third embodiment of the invention, FIG. 7a shows a cross-section through the jaws opening adjustment mechanism, for the second output angle—one of the pre-set jaws opening position B (corresponding to FIG. 7), for the third embodiment of the invention, FIG. 7b shows a view of the clipping machine handgrip part from the gripping side of the shutter element for the pre-set jaws opening adjustment mechanism for the first second angle—one of the pre-set jaws opening position B (corresponding to FIG. 7a), for the third embodiment of the invention, FIG. 8 shows an axonometric view of the shutter element for the third embodiment of the invention, FIG. 8a shows a perspective view of the shutter element for the third embodiment of the invention FIG. 9 shows the clipping machine with elements shown from the outside with the rotational mechanism shown—the knob to rotate the stem with jaws, for the first and second embodiment of the invention, FIG. 10 shows a cross-section through the clipping machine as for the first and second embodiment of the invention and its individual parts with an additional rotational mechanism shown—the knob to rotate the stem with jaws, FIG. 10a shows a detail of cross-section through the clipping machine as for the first and second embodiment of the invention (from FIG. 10) in terms of the adjustment mechanism and with an additional rotational mechanism shown—the knob to rotate the stem with jaws, FIG. 11 shows the clipping machine with elements shown from the outside as for the third embodiment of the invention with an additional rotational mechanism shown—the knob to rotate the stem with jaws, FIG. 12 shows a cross-section through the clipping machine and its individual parts as for the third embodiment of the invention with an additional rotational mechanism shown—the knob to rotate the stem with jaws, FIG. 12a shows a cross-sectional detail through the clipping machine (from FIG. 12) as for the third embodiment of the invention with an additional adjustment mechanism and with a rotational mechanism shown—the knob to rotate the stem with jaws, for the third embodiment of the invention.

Figure 13A:
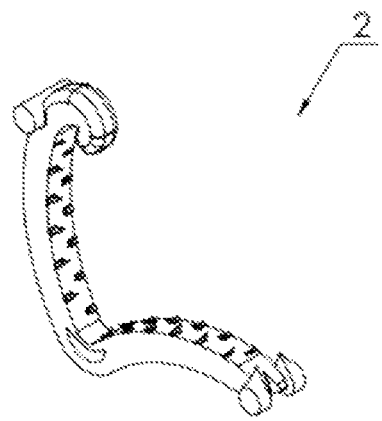
Figure 13B:
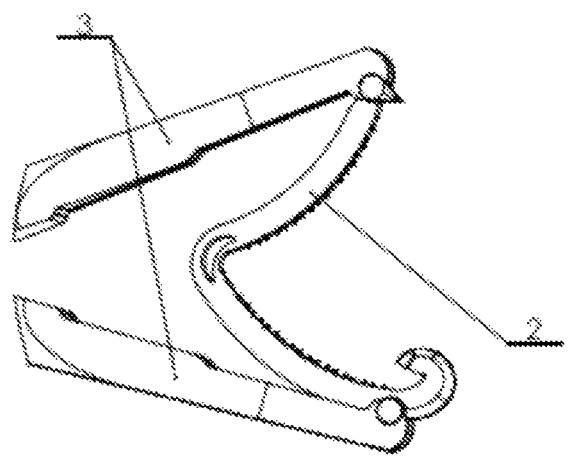

FIG. 13a shows a perspective view of the clip FIG. 13b shows the jaws with the clip attached.

EXAMPLE 1

As shown in FIGS. 1 and 2a, the laparoscopic clipping machine 1 for application of clips 2 on tissue structures, enclosed in a housing 5, comprises a pair of movable jaws 3 mounted on the stem 4, whose operational movement for clamping the clips 2 is indirectly triggered by a movement of the handle in the handgrip 7. The clipping machine comprises a luer lock 39 connector. This connector is defined by a standard and is used in the case of the clipping machine to clean internal components. The handle 7 is embedded in the housing, the spring 38 of the handgrip directly affects the handle 7, and the handle 7 affects the pusher 6. The mechanism directly triggering the operational movement of the jaws 3 comprises the pusher 6 movably arranged in axis of the stem 4 supported in axis of the stem 4 on the spring 8. As shown in FIG. 2b, the handgrip is provided with two handles—movable pulling handle 34 and fixed handle 35. Movement of the moving handle in the handgrip triggers an operational movement of the jaws 3 through the pulling handle and then through the pushers. The pair of springs is responsible for proper tension of pulling handle 34 relative to fixed handle 35—several springs can be made—spring 38 of handle and spring 8 in stem 4.

As shown in FIG. 2c, the clipping machine comprising the jaws 3 output opening adjustment mechanism 9 in the range of jaws position change for the output angle 10—change of the output angle 10 to at least two angles 10a and 10b-positions A and B of the jaws.

As mentioned, generally, the adjustment mechanism 9 is the movable shutter element 11 with gradually changing or stepping shape. In general embodiment, the adjustment mechanism 9 comprising the narrower part 12 of the shutter element and the wider part 13 of the shutter element—for example marked in FIG. 5b, which is moved in the through opening 14 light made in the pusher. The through opening 14 made transversely in the pusher is larger than the wider part 13 of the shutter element 11. Model positions A and B shown in the figures show two possible pre-sets of the shutter element 11. Model position (setting) A—when the narrower part 12 of the shutter element is introduced into the through opening 14 light of the pusher 6; model position B (setting)—when the wider part 13 of the shutter element is introduced into the through opening 14 light of the pusher 6.

The narrower part 12 and the wider part 13 of the shutter element 11 have a shape adapted to the through opening 14 made in the pusher 6, so that by placing a given part in the through opening 14 light it partially covers the light to varying degrees depending on which part of the element is in the opening 14 light. Entering a given part causes a restriction in the movement of the pusher through the handle and thus changes the output spacing of the jaws 3 by a given output angle, e.g. 10a and 10b. Due to such a construction, partially limited longitudinal movement of the pusher 6 is obtained, resulting in the output angle 10 to change and the first output angle 10a is obtained (model position A), and after passing the wider part 13 of the shutter element 11 and its location in the through opening 14 light of the pusher 6 a significantly limited longitudinal movement of pusher 6 is obtained, resulting in the second output angle 10b (model position B). In one embodiment, this is illustrated in FIGS. 3a-d and 4a-d.

The output angle 10 is adapted to two different sizes of the clips 2. For specific embodiment of the invention, these are the so-called L and XL clips from among those available on the market. In other embodiment of the adjustment mechanism 9, there may be several variations in the output angle 10—more different positions of the jaws 3 output opening—several possible output angles 10 between the jaws 3 that are matched to different surgical clips.

Preferably, the jaws 3 output opening is changed to other output positions by depressing the pulling handle 34, which releases spring tension, and simultaneously moves the adjustment mechanism 9. Changing the jaws 3 output opening can also be done without pressing the pulling handle 34, but this is difficult.

If the adjustment mechanism 9 is in the position for the second output angle 10b, then preferably the return to the first output angle 10a is realized by pressing the pulling handle 34 and sliding out/unscrewing from the through opening 14 of the shutter element 11 so that (again) its narrower part 12 covers the through opening 14 light. This position can also be changed without pressing the pulling handle 34, but this is difficult.

Pushing out the adjustment mechanism 9 will reverse the pusher 6. The pusher can be made in several parts—inner handle pusher, inner stem pusher—the first pusher 26 and the second pusher 27, shown in FIG. 2b, as described in detail in Example 5.

As shown in FIG. 5c, in an embodiment, the through opening 14 is oval in longitudinal cross-section, where the oval is characterised by a shorter diameter 15 and a longer diameter 16, where the longer diameter 16 of the oval is directed along the axis of the pusher 6 and the shorter diameter 15 of the oval is perpendicular to the pusher 6 axis and then longer diameter 16 of the oval is longer than the widest part of the shutter element 11.

The through opening 14 may have a shape other than that described above. For example, it may be similar to a rectangle.

FIG. 13a shows a perspective view of a clip 2 and FIG. 13b shows a clip 2 located in the jaws 3 of the clipping machine 1. The clip 2 attached in such a way, with defined jaws 3 output opening, as a result of their clamping operational movement indirectly triggered by movement of the handle 7, is clamped on tissue structure.

EXAMPLE 2

The clipping machine in the first embodiment is constructed as described in examples 1 and 2a-c, as shown in detail in FIGS. 3a-d and 4a-d for the position of the jaws output opening, A and B respectively, and in FIG. 5a. In this embodiment, the movable shutter element 11 is a shaped profile comprising two parts of different width in longitudinal cross-section. As shown in FIG. 5a, these parts have a shape of the first cylinder 17a extending on one side into the cone 17b with a diameter increasing in relation to the diameter of the second cylinder 17c and then extending into the second cylinder 17c.

Both parts of the shutter element 11, which are positioned in the through opening 14 light, end with bases wider than width of each part of the cylinder and/or cone—upper 36 and lower 37 base. These bases are the stop for movement of the shutter element 11 in the through opening 14. The shutter element 11 is partly guided in the first sleeve 18 made in the housing 5 of the stem 4. A threaded connection is formed on the side surface 19 of the second cylinder 17c extending through the first sleeve 18 and on the inner surface 20 of the first sleeve 18. Due to this, the shutter element 11 is gradually screwed into the through opening 14, so that the shutter element 11 is screwed into the first sleeve 18 passing through the through opening 14 made in the pusher 6. Further gradual screwing causes the second cylinder 17c to be screwed into the first sleeve 18 passing through the through opening 14 made in the pusher 6. Depending on, which part of the shutter element covers the through opening 14 light, after passing through the through opening 14 light of the first cylinder 17a, a partially limited longitudinal movement of the pusher 6 is obtained, resulting in the first output angle 10a-FIG. 3a-d, and after screwing the second cylinder 17c in the first sleeve 18 and its passage through the through opening 14 light results a significantly limited longitudinal movement of the pusher 6 is obtained, resulting in the second output angle 10b-FIGS. 4a-4d. After passing through the through opening 14 of the cone 17b part, the output angle 10 having a value between the first and second output angles 10a and 10b is obtained. Movement of the handle 7, therefore, and the movement of the pusher 6 operate within the range defined by the limit of movability determined by covering a given part of the shutter element 11 within through opening 14 light.

For this embodiment of the invention, operation of the adjustment mechanism 9 is illustrated in detail in FIG. 3a-d and FIG. 4a-d. FIG. 3a, the jaws 3 output opening at the first output angle 10a and FIG. 3b shows approximately the adjustment mechanism 9 in the pre-set imparting the jaws 3 output opening (position A) at the first output angle 10a. In FIG. 3b the shutter element 11 is shown when—generally narrower part 12, and more specifically for this embodiment—the first cylinder 17a, as in FIG. 3c, covers the pusher 6 through opening 14. FIG. 3d shows how the first cylinder 17a covers the through opening 14 light. Because the through opening 14 light is partly covered (slightly), the pusher 6 is initially pre-set so as to give a significant jaws 3 output opening (position A) at the first angle 10a. The location of the through element 11 for this position A in the through opening 14 is shown in cross-section by the adjustment mechanism 11 in FIG. 3c and longitudinally cross-section through the pusher in FIG. 3d.

In turn, FIG. 4a shows the jaws 3 output opening (position B) at the second output angle 10b and FIG. 4b shows approximately the adjustment mechanism 9 in a position giving the jaws 3 output opening at the second output angle 10b. In FIG. 4b the shutter element 11 is shown when—generally the wider part 13, and more specifically for this embodiment—the cone 17b or with further screwing of the shutter element 11 (as above), the second cylinder 17c, as in FIG. 4c, covers the through opening 14 light of the pusher 6. FIG. 4d shows how the second cylinder 17c limits the through opening 14 light. Because the through opening 14 light is significantly covered—more than in the previous position A, due to the larger diameter of the second cylinder 17c relative to the first cylinder 17a, the pusher 6 is initially pre-set so that it gives a smaller jaws 3 output opening (position B) at the second output angle 10b. The location of the through element 11 for this position B in the through opening 14 is shown in cross-section by the adjustment mechanism in FIG. 4c and longitudinally cross-section through the pusher in FIG. 4d.

For this embodiment of the invention, it is possible to pre-set the jaws 3 output opening for a plurality of output angles 10. This is possible due to the construction of the shutter element 11, where depending on which part: the first cylinder 17a, the cone 17b, or the second cylinder 17c, covers the through opening 14 light of the pusher 6, this results in a different jaws 3 output opening resulting in different output angles 10. It should be noted that the cone 17b contains a larger number of sizes (diameters) that may, more or less, cover the through opening 14 light.

EXAMPLE 3

The clipping machine in the second embodiment is constructed as described in examples 1 and 2a-c, as shown in detail in FIGS. 3a-c and 4a-c for the position of the jaws output opening A and B and in FIG. 5b. In this embodiment, the movable shutter element 11 is in a form of the third cylinder 21a connected to the fourth cylinder 21b with a larger diameter relative to the third cylinder 21a. One part located in the through opening 14 light is ended with the base 36. The shutter element 11 is screwed into the first sleeve 18 made in the housing 5 as described in example 2. The fourth cylinder 21b is movably located in the first sleeve 18 made in the housing 5 of the stem 4 and on the side surface 19 of the fourth cylinder 21b passing through the first sleeve 18 and on the inner surface 20 of the first sleeve 18 a threaded connection is formed which allows the shutter element 11 to be gradually screwed into the through opening 14 light. During gradual screwing, a part of the fourth cylinder 21b is screwed into the first sleeve 18 passing through the through opening 14 made in the pusher 6. After passing through the through opening 14 light of the pusher 6 part of the third cylinder 21a, a partially limited longitudinal movement of the pusher 6 is obtained, resulting in the first output angle 10a, and after screwing the part of the fourth cylinder 21b and its passing through the through opening 14 light of the pusher 6, a significantly limited longitudinal movement of the pusher 6 is obtained, resulting in the second output angle 10b-shown respectively in FIGS. 3a-d and 4a-d and as discussed above.

The difference between the clipping machine according to example 2 and 3 is that, the shutter element 11 according to the second embodiment (example 3) has only two parts 12 and 13 (specifically 21a and 21b) which can more or less covers the through opening 14 light of the pusher 6, giving only two possible output angles 10: 10a and 10b. In case of the first embodiment (example 2), part of the cone 17b allows to obtain more jaws 3 output openings, i.e. output angles 10 (10a, 10b and other angles 10 between angles 10a and 10b).

EXAMPLE 4

In the third embodiment, the clipping machine is constructed as described in example 1, as shown in detail in FIGS. 6, 6a and 6b and FIGS. 7, 7a and 7b for the position of the jaws output openings A and B, respectively, and in FIGS. 8 and 8a. In this embodiment, the movable shutter element 11 shown in FIG. 8 and FIG. 8a essentially comprises the gripping part 22 mounted on the housing 5 of the clipping machine 1 and the shutter part 23 permanently connected to the gripping part 22 to obtain an L-shaped cross-section. The shutter part 23 passes through the through opening 14 light of the pusher 6. The shutter part 23 has a shape of a cam with width 24 and height 25 relative to the width of the through opening 14. The shutter part 23 is movably guided by means of the gripping part 22 in the through opening 14 of the pusher 6. Both elements are connected by means of a cylinder—sleeve. After passing through the through opening 14 light of the pusher 6 of the shutter part 23, the width 24 of the shutter part 23 covers the through opening 14 light, and the partially longitudinal limited movement of the pusher 6 is obtained, resulting in the first output angle 10a-FIGS. 6, 6a and 6b. After rotating the shutter element 23, using the gripping part 22 of the shutter element 11, height 25 of the shutter part 22 covers the through opening 14 light and then the significantly limited longitudinal movement of the pusher 6 is obtained, resulting in the second output angle 10b—FIGS. 7, 7a and 7b.

FIGS. 6, 6a and 6b shows in detail position of the shutter element 11 in the through opening 14 light of the pusher 6. When the gripping part 22 is located along the axis of the clipping machine (pusher 6), then the cam forming shutter part 23 covers the through opening 14 light slightly over its longer diameter 16, if it was an oval, slightly blocking the movement of the pusher 6 and giving the output angle 10a as shown in FIG. 6. If the operator turns the shutter element 11, using the gripping part 22, changing its position perpendicular to the axis of the clipping machine (pusher 6)—as in FIG. 7b, so that the cam forming shutter part 23 covers the through opening 14 light considerably on its longer diameter 16 if it was an oval, the cam in this arrangement significantly blocks the movement of the pusher 6—as in FIG. 7a, and this pre-set evokes the second output angle 10b as shown in FIG. 7.

For such construction of the shutter element 11 as in the third embodiment, it is possible to obtain preferably two possible output angles 10: 10a and 10b.

EXAMPLE 5

The clipping machine is constructed as described in example 1-4 and is shown in FIGS. 9-12, except that the clipping machine comprises at least two movably connected pushers 6 to each other: the first pusher 26 at handle 7 height and the second pusher 27 extending into the stem 4 with the jaws 3 and directly triggering the jaws 3 to move. One end of the first pusher 26 has a spherical seat 28 and the end of the second pusher 27 connected to it has the sphere 29 matching the seat 28 allowing the movement of the second pusher 27 relative to the first pusher 26. At a height of said connection of the two pushers 6 there is the rotational mechanism 30 causing rotation of the second pusher 27 and the stem 4 relative to the first pusher 26 consisting the knob 31 to cause a rotation of the second pusher 27 and stem 4 relative to the first pusher 26, the second sleeve 32 with the knob 31, to which the stem 4 is connected. The control of the jaws output opening mechanism takes place as described above—the rotational mechanism 30 operates independently of the jaws 3 output opening adjustment mechanism 9. Turning the knob with hand causes rotation of the second sleeve 32 permanently connected to the knob 31, rotation of the stem 4 and the second pusher 27 and the pair of jaws 3. Luer lock 39 is located in the knob 31 and can be considered as part of the rotation element, although it does not affect the rotation in any way.

This example of the invention is shown in FIG. 9, FIG. 10 and FIG. 10a, which shows the first and second embodiments (examples 2 and 3) of the invention with the additional rotational mechanism 30.

In turn, FIG. 11, FIG. 12 and FIG. 12a shows the third embodiment of the invention (example 4) with the additional rotational mechanism 30 as described above.

LIST OF REFERENCE NUMBERS

1—laparoscopic clipping machine
2—clip
3—jaws
4—stem
5—housing
6—pusher
7—handle
8—spring
9—adjustment mechanism
10—output angle
10a—first output angle
10b—second output angle
11—shutter element
12—narrower part of the shutter element (11)
13—wider part of the shutter element (11)
14—through opening
15—shorter oval diameter
16—longer oval diameter
17a—first cylinder
17b—cone
17c—second cylinder 18—first sleeve
19—lateral surface of the second cylinder
20—inner surface of the first sleeve (18)
21a—third cylinder
21b—fourth cylinder
22—gripping part
23—shutter part of the shutter element (11)
24—width of the shutter part (22)
25—height of the shutter part (22)
26—first pusher
27—second pusher
28—seat
29—sphere
30—rotational mechanism
31—knob
32—second sleeve
33—internal spring
34—pulling handle
35—fixed handle
36—upper base
37—lower base
38—handle spring
39—luer lock connector

The invention claimed is:

1. A laparoscopic clipping machine for application of clips on tissue structures, enclosed in a housing, comprising:
 a pair of movable jaws mounted on a stem, whose operational movement for clamping the clips is indirectly triggered by movement of a handle,
 at least one spring,
 a mechanism directly triggering operational movement of the jaws including at least one pusher movably arranged along an axis of the stem supported in the axis of the stem on the at least one spring,
 an adjustment mechanism that adjusts the jaws output opening to at least two positions of the output opening adapted to receive at least two sizes of the clips, resulting in an output angle between the jaws, the adjustment mechanism including:
  a movable shutter element having at least two parts, including a narrower part of the shutter element and a wider part of the shutter element, and the shutter element is movably guided through a through opening laterally formed in the at least one pusher, wherein the through opening is larger than the wider part of the shutter element such that the shutter element, when seated in the through opening, partially covers the through opening, thus limiting the movement of the at least one pusher when determining the output angle, in such a way, that when the narrower part of the shutter element is positioned within the through opening, a partially limited longitudinal movement of the at least one pusher is obtained, resulting in a first output angle, and when the wider part of the shutter element is positioned within the through opening, a further limited longitudinal movement of the at least one pusher is obtained, resulting in the second output angle.

2. The clipping machine according to claim 1, wherein:
the through opening is oval in the longitudinal cross-section,
the oval has a shorter diameter and a longer diameter, and
the longer diameter of the oval is directed along the axis of the at least one pusher and the shorter diameter of the oval is perpendicular to the at least one pusher axis and the longer diameter of the oval is longer than the widest part of the shutter element.

3. The clipping machine according to claim 2, wherein:
the movable shutter element comprises a first cylinder extending on one side into a cone with a diameter increasing in relation to the diameter of a second cylinder and further extending into the second cylinder, wherein the second cylinder is partly guided in a first sleeve of the stem, and
a threaded connection is formed on the lateral surface of the second cylinder extending through the first sleeve and on the inner surface of the first sleeve such that the shutter element is screwed into the first sleeve by passing through the through opening, in such a way, that the second cylinder is screwed into the first sleeve passing through the through opening, such that, when the first cylinder passes through the through opening, the partially limited longitudinal movement of the at least one pusher is obtained, resulting in the first output angle, when the second cylinder is screwed into the first sleeve and positioned through the through opening, the further limited longitudinal movement of the at least one pusher is obtained, resulting in the second output angle, and when the cone is positioned within the through opening, the output angle is a value between the first output angle and second output angle.

4. The clipping machine according to claim 3, wherein the at least one pusher comprises:
at least two movably connected pushers connected to each other, the first pusher positioned at the top of the handle and the second pusher extending into the stem, wherein:
 one end of the first pusher has a spherical seat and one end of the second pusher has a sphere matching the seat such that the sphere is connected to the seat, and at the connection of the first and second pushers there is a rotational mechanism configured to cause a rotation of the second pusher and the stem relative to the first pusher, wherein the rotational mechanism comprises a knob and a second sleeve connected to the stem.

5. The clipping machine according to claim 2, wherein the at least one pusher comprises:
at least two movably connected pushers connected to each other, the first pusher positioned at the top of the handle and the second pusher extending into the stem, wherein:
 one end of the first pusher has a spherical seat and one end of the second pusher has a sphere matching the seat such that the sphere is connected to the seat, and at the connection of the first and second pushers there is a rotational mechanism configured to cause a rotation of the second pusher and the stem relative to the first pusher, wherein the rotational mechanism comprises a knob and a second sleeve connected to the stem.

6. The clipping machine according to claim 1, wherein:
the movable shutter element comprises a third cylinder connected to a fourth cylinder with a larger diameter relative to the third cylinder,
wherein the fourth cylinder is movably arranged in a first sleeve of the stem, and
a threaded connection is formed on the lateral surface of the fourth cylinder extending through the first sleeve and on the inner surface of the first sleeve, such that a part of the fourth cylinder is screwed into the first sleeve passing through the through opening, such that, when the third cylinder is positioned within the through opening, the partially limited longitudinal movement of the at least one pusher is obtained, resulting in the first output angle, and when the part of the fourth cylinder is screwed into the first sleeve and positioned within the through opening, further limited longitudinal movement of at least one pusher is obtained, resulting in the output second angle.

7. The clipping machine according to claim 6, wherein the at least one pusher comprises:
at least two movably connected pushers connected to each other, the first pusher positioned at the top of the handle and the second pusher extending into the stem, wherein:
one end of the first pusher has a spherical seat and one end of the second pusher has a sphere matching the seat such that the sphere is connected to the seat, and at the connection of the first and second pushers there is a rotational mechanism configured to cause a rotation of the second pusher and the stem relative to the first pusher, wherein the rotational mechanism comprises a knob and a second sleeve connected to the stem.

8. The clipping machine according to claim 1, wherein:
the movable shutter element comprises a gripping part mounted on the clipping machine housing and a shutter part permanently connected to the gripping part wherein the shutter part passes through the through opening, and
wherein the shutter part has the shape of a cam with a width and a height, wherein the shutter part is movably guided, by means of the gripping part, into the through opening, such that, when the shutter part is positioned within and through opening in such a way that the width of the shutter part covers the through opening, the partially limited longitudinal movement of the at least one pusher is obtained, resulting in the first output angle, and when the shutter element is rotated using the gripping part such that the height of the shutter part covers the through opening, the further limited longitudinal movement of the at least one pusher is obtained, resulting in the second output angle.

9. The clipping machine according to claim 8, wherein the at least one pusher comprises:
at least two movably connected pushers connected to each other, the first pusher positioned at the top of the handle and the second pusher extending into the stem, wherein:
one end of the first pusher has a spherical seat and one end of the second pusher has a sphere matching the seat such that the sphere is connected to the seat, and at the connection of the first and second pushers there is a rotational mechanism configured to cause a rotation of the second pusher and the stem relative to the first pusher, wherein the rotational mechanism comprises a knob and a second sleeve connected to the stem.

10. The clipping machine according to claim 1, wherein the at least one pusher comprises:
at least two movably connected pushers connected to each other, the first pusher positioned at the top of the handle and the second pusher extending into the stem, wherein:
one end of the first pusher has a spherical seat and one end of the second pusher has a sphere matching the seat such that the sphere is connected to the seat, and at the connection of the first and second pushers there is a rotational mechanism configured to cause a rotation of the second pusher and the stem relative to the first pusher, wherein the rotational mechanism comprises a knob and a second sleeve connected to the stem.

11. The clipping machine according to claim 1, wherein:
the movable shutter element comprises the first cylinder extending on one side into cone with a diameter increasing in relation to the diameter of the second cylinder and further extending into the second cylinder, wherein the second cylinder is partly guided in the first sleeve of the stem, and
a threaded connection is formed on the lateral surface of the second cylinder extending through the first sleeve and on the inner surface of the first sleeve such that the shutter element is screwed into the first sleeve by passing through the through opening, in such a way, that the second cylinder is screwed into the first sleeve passing through the through opening, such that, when the first cylinder passes through the through opening, the partially limited longitudinal movement of the at least one pusher is obtained, resulting in the first output angle, when the second cylinder is screwed into the first sleeve and positioned through the through opening, the further limited longitudinal movement of the at least one pusher is obtained, resulting in the second output angle, and when the cone is positioned within the through opening, the output angle is a value between the first output angle and second output angle.

12. The clipping machine according to claim 11, wherein the at least one pusher comprises:
at least two movably connected pushers connected to each other, the first pusher positioned at the top of the handle and the second pusher extending into the stem, wherein:
one end of the first pusher has a spherical seat and one end of the second pusher has a sphere matching the seat such that the sphere is connected to the seat, and at the connection of the first and second pushers there is a rotational mechanism configured to cause a rotation of the second pusher and the stem relative to the first pusher, wherein the rotational mechanism comprises a knob and a second sleeve connected to the stem.

13. The clipping machine according to claim 12, wherein:
the movable shutter element comprises a third cylinder connected to the fourth cylinder with a larger diameter relative to the third cylinder,
wherein the fourth cylinder is movably arranged in the first sleeve of the stem, and
a threaded connection is formed on the lateral surface of the fourth cylinder extending through the first sleeve and on the inner surface of the first sleeve, such that a part of the fourth cylinder is screwed into the first sleeve passing through the through opening, such that, when the third cylinder is positioned within the through opening, the partially limited longitudinal movement of the at least one pusher is obtained, resulting in the first output angle, and when the part of the fourth cylinder is screwed into the first sleeve positioned within the through opening, further limited longitudinal movement of the at least one pusher is obtained, resulting in the output second angle.

14. The clipping machine according to claim 13, wherein the at least one pusher comprises:
at least two movably connected pushers connected to each other, the first pusher positioned at the top of the handle and the second pusher extending into the stem, wherein:

one end of the first pusher has a spherical seat and one end of the second pusher has a sphere matching the seat such that the sphere is connected to the seat, and at the connection of the first and second pushers there is a rotational mechanism configured to cause a rotation of the second pusher and the stem relative to the first pusher, wherein the rotational mechanism comprises a knob and a second sleeve connected to the stem.

\* \* \* \* \*